US012064236B2

(12) United States Patent
Hossein Yazdi et al.

(10) Patent No.: US 12,064,236 B2
(45) Date of Patent: Aug. 20, 2024

(54) METHODS, SYSTEMS, AND DEVICES FOR IMPROVED SENSORS FOR CONTINUOUS GLUCOSE MONITORING

(71) Applicant: MEDTRONIC MINIMED, INC., Northridge, CA (US)

(72) Inventors: Soroush Hossein Yazdi, Laguna Niguel, CA (US); Melissa Tsang, Sherman Oaks, CA (US); Ellis Garai, Studio City, CA (US); Sadaf S. Seleh, Encino, CA (US); Steven Lai, Granada Hills, CA (US); Luis A. Torres, South Gate, CA (US); Bradley Petkus, Sherman Oaks, CA (US); Xin Heng, Glendale, CA (US); Zhenzhong Sun, Northridge, CA (US); Akhil Srinivasan, Woodland Hills, CA (US); Tyler R. Wong, Pasadena, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 249 days.

(21) Appl. No.: 16/898,941

(22) Filed: Jun. 11, 2020

(65) Prior Publication Data
US 2021/0386331 A1    Dec. 16, 2021

(51) Int. Cl.
*A61B 5/145*    (2006.01)
*A61B 5/00*     (2006.01)
*A61B 5/1486*   (2006.01)
*G16H 20/10*    (2018.01)

(52) U.S. Cl.
CPC ........ *A61B 5/14532* (2013.01); *A61B 5/1486* (2013.01); *A61B 5/4848* (2013.01); *A61B 5/7203* (2013.01); *G16H 20/10* (2018.01)

(58) Field of Classification Search
CPC . A61B 5/14532; A61B 5/1486; A61B 5/4848; A61B 5/7203; A61B 5/14865; G16H 20/10
See application file for complete search history.

(56) References Cited

U.S. PATENT DOCUMENTS

| | | |
|---|---|---|
| 4,562,751 A | 1/1986 | Nason et al. |
| 4,573,994 A | 3/1986 | Fischell et al. |
| 4,678,408 A | 7/1987 | Nason et al. |
| 4,685,903 A | 8/1987 | Cable et al. |
| 4,755,173 A | 7/1988 | Konopka et al. |
| 5,391,250 A | 2/1995 | Cheney, II et al. |

(Continued)

OTHER PUBLICATIONS

International Search Report and Written Opinion of the International Searching Authority issued in corresponding application PCT/US2021/033957 mailed Aug. 26, 2021 (13 pages).

*Primary Examiner* — Yi-Shan Yang
*Assistant Examiner* — Kyle W. Kretzer
(74) *Attorney, Agent, or Firm* — Carter, DeLuca & Farrell LLP

(57) ABSTRACT

Methods, systems, and devices for continuous glucose monitoring. More particularly, the methods, systems, and devices describe a working electrode with a GOx sensor and a background electrode in which the background electrode has no GOx sensor. The system may then compare the first signal and the second signal to detect ingestion of a medication by the user. The system may generate a sensor glucose value based on the comparison.

9 Claims, 10 Drawing Sheets

(56) References Cited

U.S. PATENT DOCUMENTS

| | | |
|---|---|---|
| 5,482,473 A | 1/1996 | Lord et al. |
| 5,485,408 A | 1/1996 | Blomquist |
| 5,522,803 A | 6/1996 | Teissen-Simony |
| 5,660,163 A | 8/1997 | Schulman et al. |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2010/0030045 A1* | 2/2010 | Gottlieb ............ A61B 5/1473 600/347 |
| 2010/0160861 A1 | 6/2010 | Causey, III et al. |
| 2017/0181677 A1* | 6/2017 | Varsavsky ............ A61B 5/7203 |
| 2019/0175082 A1 | 6/2019 | Varsavsky et al. |
| 2019/0328297 A1* | 10/2019 | Boo .................... A61B 5/1473 |
| 2019/0357827 A1* | 11/2019 | Li ...................... A61B 5/14503 |
| 2020/0000386 A1 | 1/2020 | Gupta et al. |

\* cited by examiner

METHODS, SYSTEMS, AND DEVICES FOR IMPROVED SENSORS FOR CONTINUOUS GLUCOSE MONITORING

FIELD

The present technology is generally related to sensor technology, including sensors used for sensing a variety of physiological parameters, e.g., glucose concentration.

BACKGROUND

Over the years, a variety of sensors have been developed for detecting and/or quantifying specific agents or compositions in a patient's blood, which enable patients and medical personnel to monitor physiological conditions within the patient's body. Illustratively, subjects may wish to monitor blood glucose levels in a subject's body on a continuing basis. Thus, glucose sensors have been developed for use in obtaining an indication of blood glucose levels in a diabetic patient. Such readings are useful in monitoring and/or adjusting a treatment regimen which typically includes the regular administration of insulin to the patient. Presently, a patient can measure his/her blood glucose ("BG") using a BG measurement device (i.e., glucose meter), such as a test strip meter, a continuous glucose measurement system (or a continuous glucose monitor), or a hospital BG test. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device.

SUMMARY

Current continuous glucose measurement systems include subcutaneous (or short-term) sensors and implantable (or long-term) sensors. Sensors have been applied in a telemetered characteristic monitor system. A telemetered system using an electrochemical sensor includes a remotely located data receiving device, a sensor for producing signals indicative of a characteristic of a user, and a transmitter device for processing signals received from the sensor and for wirelessly transmitting the processed signals to the remotely located data receiving device. The data receiving device may be a characteristic monitor, a data receiver that provides data to another device, an RF programmer, a medication delivery device (such as an infusion pump), or the like. Regardless of whether the data receiving device (e.g., a glucose monitor), the transmitter device, and the sensor (e.g., a glucose sensor) communicate wirelessly or via an electrical wire connection, a characteristic monitoring system of the type described above is of practical use only after it has been calibrated based on the unique characteristics of the individual user.

Continuous glucose monitoring ("CGM") is largely adjunctive, meaning that the readings provided by a CGM device (including, e.g., an implantable or subcutaneous sensor) cannot be used without a reference value in order to make a clinical decision. The reference value, in turn, must be obtained from a finger stick using, e.g., a BG meter. The reference value is needed because there is a limited amount of information that is available from the sensor/sensing component. Generally, glucose measurements are based on interactions with one of three enzymes: hexokinase, glucose oxidase ("GOx") or glucose-1-dehydrogenase ("GDH").

Specifically, the only pieces of information that are currently provided by the sensing component for processing are the raw sensor value (i.e., the sensor current or Isig) and the counter voltage. Therefore, during analysis, if it appears that the raw sensor signal is abnormal (e.g., if the signal is decreasing), the only way one can distinguish between a sensor failure and a physiological change within the user/patient (i.e., glucose level changing in the body) is by acquiring a reference glucose value via a finger stick. However, the use of repeated finger sticks by a user/patient is painful and otherwise undesirable; therefore, methods, systems, and devices are described herein to minimize the amount of testing and/or calibrations necessary for CGM and improve their reliability through improvements to glucose oxidase ("GOx") sensors.

To further compound the hurdles faced by CGM devices, government agencies (e.g., the Federal Drug Administration ("FDA")) impose restrictions and requirements for the sensitivity of CGMs to various medications. For example, CGM devices are required to have minimal impact from exposure to acetaminophen (a commonly used treatment for minor pain relief) when orally taken by a user per the FDA iCGM special requirements. GOx is a standard enzyme for biosensors as it has a relatively higher selectivity for glucose. GOx is also easy to obtain, inexpensive, and can withstand greater extremes of pH, ionic strength, and temperature than many other enzymes, thus allowing less stringent conditions during the manufacturing process and relatively relaxed storage norms for use by lay biosensor users. However, traditional GOx sensors are impacted by the presence of acetaminophen, which could results in an error in an estimated BG based on the sensor glucose ("SG") signal. For example, a high dose of acetaminophen can generate analytical interference on electrochemical biosensors because acetaminophen is directly oxidized after diffusing across a porous membrane to the electrode surface, producing an interfering current that increases the glucose reading. Accordingly, methods, systems, and devices are described herein to further improve on the reliability of CGM devices and GOx sensors through improvements to detect the presence of acetaminophen in a GOx sensors and/or improvements on how to correct the measured SG signal being calculated.

More particularly, the methods, systems, and devices describe a working electrode with a GOx sensor and a background electrode in which the background electrode has no GOx sensor. In some embodiments, a background electrode metallization layer may be composed of various materials. For example, the background electrode metal layer may be made of platinum, gold, or another material. In some embodiments, the electrode material and the applied voltage may be tuned to target various types of interferents. For example, a gold electrode and a voltage of 600 mV may be used for a first analyte of interest, while a carbon electrode and a voltage of 900 mV may be used for a second analyte of interest. In one embodiment, the working electrode and the background electrode may have the same operating potential. The system may then subtract the two signals from one another to remove the signal originating at the background electrode. Accordingly, in this embodiment, the system may determine a difference in the signals between the working electrode and the background electrode. If acetaminophen is used by a user/patient, only the working electrode is affected. That is, as the working electrode includes a GOx sensor, which may be impacted from exposure to acetaminophen, but the background electrode does not. The difference in the signals between the working electrode and the background electrode is then used for calculating, generating, and adjusting a sensor glucose value. In some embodiments, the signal from the working electrode and the signal from the background electrode may be input as a parameter to a pre-determined mathematical model (e.g., external calibration model) in order to adjust the sensor glucose value.

In another embodiment, the working electrode and the background electrode may have different voltage potentials (Vset) for the working electrode and the background electrode. The working electrode may be operated at a lower Vset relative for the background electrode. For example, the working electrode may be operated at 400-500 mV range while the background electrode is operated in the 500-600 mV range. For example, calculating a sensor glucose value based on the different voltage potentials (Vset) for the working electrode and the background electrode as described above provides a more accurate measure of sensor glucose values, particularly in the presence medication that produces an interfering current that increases a system reading. In some embodiments, the voltage potentials (Vset) may be stored by electronic circuitry (e.g., storage circuitry).

In some aspects, methods, systems, and devices for continuous glucose monitoring are described. For example, the system may activate a first electrode on a user, wherein the first electrode detects Glucose Oxidase (GOx). The system may activate a second electrode the user, wherein the second electrode does not detect GOx. The system may set a first voltage potential (Vset) for the first electrode. The system may set a second voltage potential (Vset) for the second electrode; receiving a first signal from the first electrode. The system may receive a second signal from the second electrode. The system may compare the first signal and the second signal to detect ingestion of a medication by the user. The system may generate a sensor glucose value based on the comparison.

Various other aspects, features, and advantages will be apparent through the detailed description and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a sub-part of, or the entirety of, a given item (e.g., data) unless the context clearly dictates otherwise.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A detailed description of embodiments of the invention will be made with reference to the accompanying drawings, wherein like numerals designate corresponding parts in the figures.

DETAILED DESCRIPTION

Figure 1:
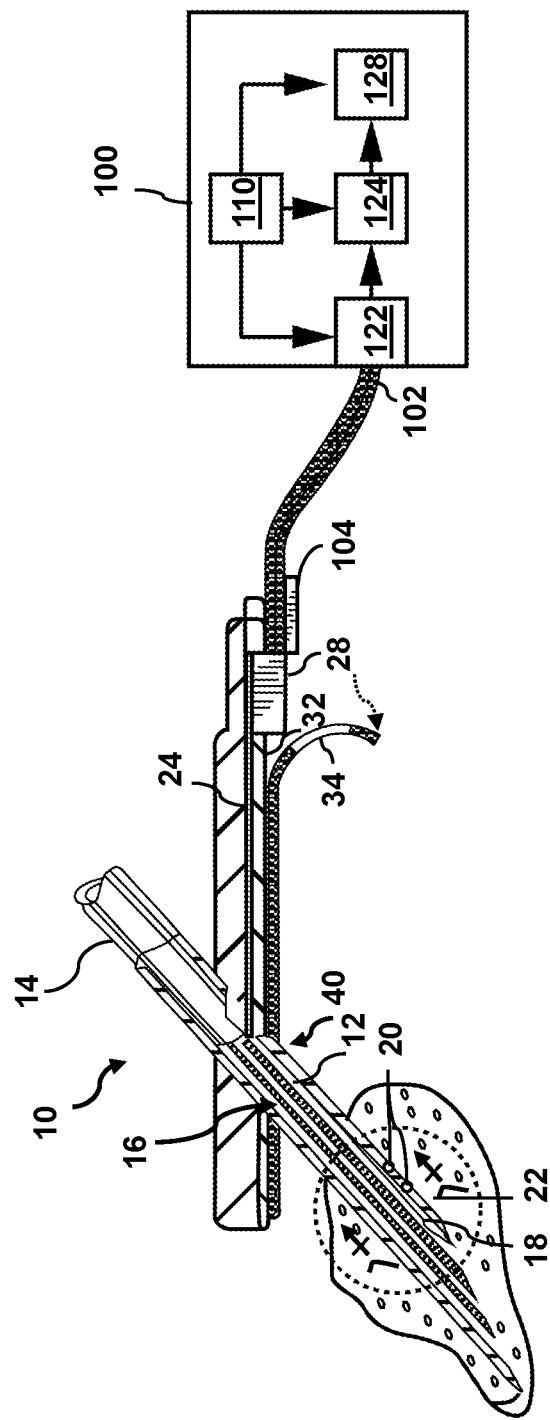
FIG. 1 is a perspective view of a subcutaneous sensor insertion set and block diagram of a sensor electronics device.

In the following description, reference is made to the accompanying drawings which form a part hereof and which illustrate several embodiments of the present inventions. It is understood that other embodiments may be utilized, and structural and operational changes may be made without departing from the scope of the present inventions.

The inventions herein are described below with reference to flowchart illustrations of methods, systems, devices, apparatus, and programming and computer program products. It will be understood that each block of the flowchart illustrations, and combinations of blocks in the flowchart illustrations, can be implemented by programing instructions, including computer program instructions (as can any menu screens described in the figures). These computer program instructions may be loaded onto a computer or other programmable data processing apparatus (such as a controller, microcontroller, or processor in a sensor electronics device) to produce a machine, such that the instructions which execute on the computer or other programmable data processing apparatus create instructions for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein. Programming instructions may also be stored in and/or implemented via electronic circuitry (e.g., storage circuitry, processing circuitry), including integrated circuits (ICs) and Application Specific Integrated Circuits (ASICs) used in conjunction with sensor devices, apparatuses, and systems. The following terms and definitions may also be used herein:

| Term | Definition |
| --- | --- |
| BG | Blood Glucose value in mg/dL typically from a fingerstick reading. Assumed use is for a sensor calibration |
| Calibrated Mode | Sensor operation mode in which the algorithm expects to receive BG calibrations as part of regular operation |
| CE | Calibration Error |
| CF (or calFactor) | Calibration Factor, sensor sensitivity to glucose used to calculate sensor glucose. Units are mg/dL/nA |
| CR (or cr) | Calibration Ratio, sensitivity based on a single BG and Isig |
| Discard | Packet flagged to be invalid based on Isig. |
| early calibration | Temporary CF update on the packet following a BG |
| EIS | Electrochemical Impedance Spectroscopy, Diagnostic capability to measure impedances at varying frequencies applied by the AFE IC |
| final calibration | Refers to updates to CF and other variables which may occur 10-15 minutes after a BG entry |
| fisig | Filtered Isig, used in calibration and SG calculation |
| GST | Glucose Sensor Transmitter |
| GOx | Glucose Oxidase |
| initialization | Sensor Initialization. This typically refers to data collection activities during sensor warm up period |
| Instant calibration error | CE check based on prior Isig, determines if a BG can be used for calibration |
| invalid packet | Refers to a packet being flagged as invalid. Packets flagged as invalid do not show SG to the user. |
| Isig | 5-minute reading of sensor current in nA. Sometimes calles "raw Isig" |
| Isig1 | 1-minute reading of sensor current in nA. Sometimes called "1-minute Isig" |
| Isig Dip | Isig Dip Calibration. Refers to logic which may adjust CF following a calibration on an abnormally low Isig |
| MAX_CR | Maximum acceptable CR |
| MIN_CR | Minimum acceptable CR |
| Not Calibrated Mode | Sensor operation mode in which the algorithm does not expect to receive BG calibrations as part of regular operations. The algorithm can utilize BG calibrations if any is made available. |
| Packet (or SG Packet or Isig Packet) | Refers to the collection of variables calculated at the 5-minute interval, including Isig, sg, ect. |
| SG | Sensor Glucose value in mg/dL |
| Vset | Voltage potential |

FIG. 1 is a perspective view of a subcutaneous sensor insertion set and a block diagram of a sensor electronics device. As illustrated in FIG. 1, a subcutaneous sensor set 10 is provided for subcutaneous placement of an active portion of a flexible sensor 12 (see, e.g., FIG. 2), or the like, at a selected site in the body of a user. The subcutaneous or percutaneous portion of the sensor set 10 includes a hollow, slotted insertion needle 14, and a cannula 16. The needle 14 is used to facilitate quick and easy subcutaneous placement of the cannula 16 at the subcutaneous insertion site. Inside the cannula 16 is a sensing portion 18 of the sensor 12 to expose one or more sensor electrodes 20 to the user's bodily fluids through a window 22 formed in the cannula 16. In one embodiment, the one or more sensor electrodes 20 may include a counter electrode, a reference electrode, and one or more working electrodes. After insertion, the insertion needle 14 is withdrawn to leave the cannula 16 with the sensing portion 18 and the sensor electrodes 20 in place at the selected insertion site.

In particular embodiments, the subcutaneous sensor set 10 facilitates accurate placement of a flexible thin film electrochemical sensor 12 of the type used for monitoring specific blood parameters representative of a user's condition. The sensor 12 monitors glucose levels in the body and may be used in conjunction with automated or semi-automated medication infusion pumps of the external or implantable type to control delivery of insulin to a diabetic patient, as described, e.g., in U.S. Pat. No. 4,562,751; 4,678,408; 4,685,903 or 4,573,994, which are herein incorporated by reference.

Particular embodiments of the flexible electrochemical sensor 12 are constructed in accordance with thin film mask techniques to include elongated thin film conductors embedded or encased between layers of a selected insulative material such as polyimide film or sheet, and membranes. The sensor electrodes 20 at a tip end of the sensing portion 18 are exposed through one of the insulative layers for direct contact with patient blood or other body fluids, when the sensing portion 18 (or active portion) of the sensor 12 is subcutaneously placed at an insertion site. The sensing portion 18 is joined to a connection portion 24 that terminates in conductive contact pads, or the like, which are also exposed through one of the insulative layers. In alternative embodiments, other types of implantable sensors, such as chemical based, optical based, or the like, may be used.

As is known in the art, the connection portion 24 and the contact pads are generally adapted for a direct wired electrical connection to a suitable monitor or sensor electronics device 100 for monitoring a user's condition in response to signals derived from the sensor electrodes 20. Further description of flexible thin film sensors of this general type are be found in U.S. Pat. No. 5,391,250, entitled METHOD OF FABRICATING THIN FILM SENSORS, which is herein incorporated by reference. The connection portion 24 may be conveniently connected electrically to the monitor or sensor electronics device 100 or by a connector block 28 (or the like) as shown and described in U.S. Pat. No. 5,482,473, entitled FLEX CIRCUIT CONNECTOR, which is also herein incorporated by reference. Thus, in accordance with some embodiments, subcutaneous sensor sets 10 may be configured or formed to work with either a wired or a wireless characteristic monitor system.

The sensor electrodes 20 may be used in a variety of sensing applications and may be configured in a variety of ways. For example, the sensor electrodes 20 may be used in physiological parameter sensing applications in which some type of biomolecule is used as a catalytic agent. For example, the sensor electrodes 20 may be used in a glucose and oxygen sensor having a glucose oxidase (GOx) enzyme catalyzing a reaction with the sensor electrodes 20. The sensor electrodes 20, along with a biomolecule or some other catalytic agent, may be placed in a human body in a vascular or non-vascular environment. For example, the sensor electrodes 20 and biomolecule may be placed in a vein and be subjected to a blood stream or may be placed in a subcutaneous or peritoneal region of the human body.

The monitor 100 may also be referred to as a sensor electronics device 100. The monitor 100 may include a power source 110, a sensor interface 122, processing electronics 124, and data formatting electronics 128. The monitor 100 may be coupled to the sensor set 10 by a cable 102 through a connector that is electrically coupled to the connector block 28 of the connection portion 24. In an alternative embodiment, the cable may be omitted. In this embodiment, the monitor 100 may include an appropriate connector for direct connection to the connection portion 104 of the sensor set 10. The sensor set 10 may be modified to have the connector portion 104 positioned at a different location, e.g., on top of the sensor set to facilitate placement of the monitor 100 over the sensor set.

In one embodiment, the sensor interface 122, the processing electronics 124, and the data formatting electronics 128 are formed as separate semiconductor chips, however, alternative embodiments may combine the various semiconductor chips into a single, or multiple customized semiconductor chips. The sensor interface 122 connects with the cable 102 that is connected with the sensor set 10.

The power source 110 may be a battery. The battery can include three series silver oxide 357 battery cells. In alternative embodiments, different battery chemistries may be utilized, such as lithium-based chemistries, alkaline batteries, nickel metal hydride, or the like, and a different number of batteries may be used. The monitor 100 provides power to the sensor set via the power source 110, through the cable 102 and cable connector 104. In one embodiment, the power is a voltage provided to the sensor set 10. In another embodiment, the power is a current provided to the sensor set 10. In an embodiment, the power is a voltage provided at a specific voltage to the sensor set 10.

Figure 2:
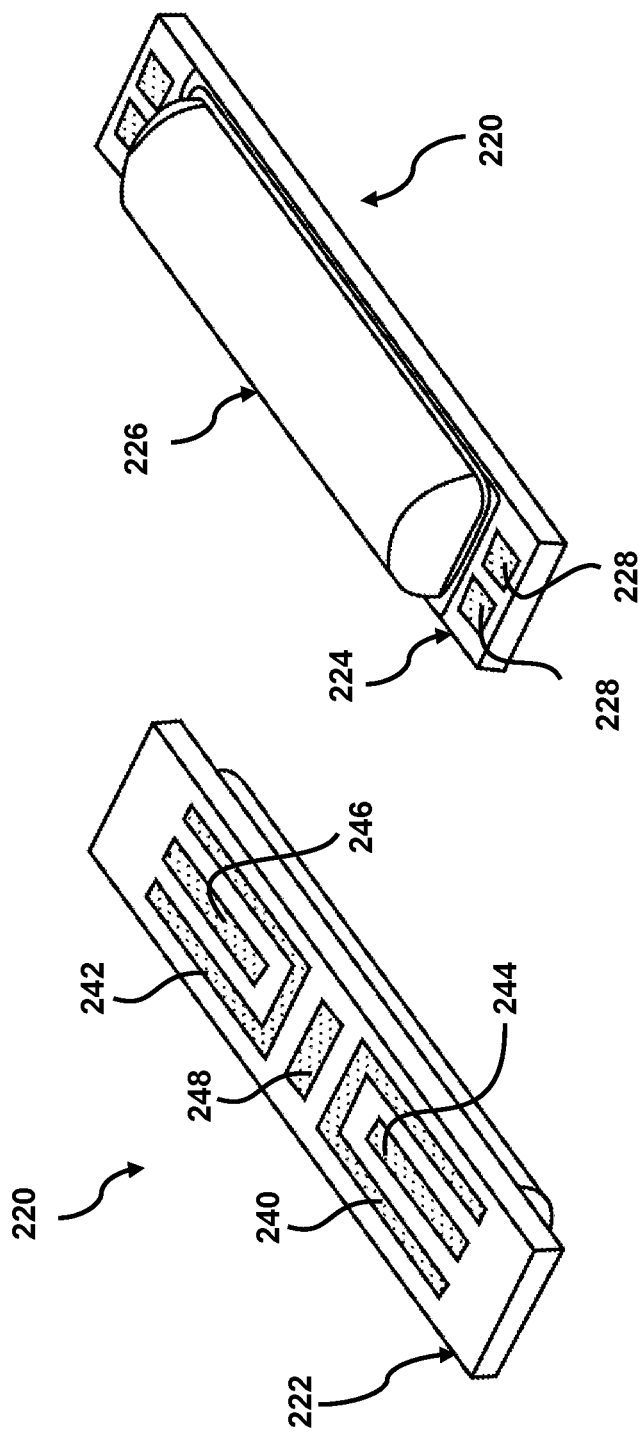
FIG. 2 illustrates a substrate having two sides, a first side which contains an electrode configuration and a second side which contains electronic circuitry.

FIG. 2 illustrates an implantable sensor, and electronics for driving the implantable sensor in accordance with one embodiment. FIG. 2 shows a substrate 220 having two sides, a first side 222 of which contains an electrode configuration and a second side 224 of which contains electronic circuitry (e.g., storage circuitry, processing circuitry, etc.). As may be seen in FIG. 2, a first side 222 of the substrate comprises two counter electrode-working electrode pairs 240, 242, 244, 246 on opposite sides of a reference electrode 248. A second side 224 of the substrate comprises electronic circuitry. As shown, the electronic circuitry may be enclosed in a hermetically sealed casing 226, providing a protective housing for the electronic circuitry. This allows the sensor substrate 220 to be inserted into a vascular environment or other environment which may subject the electronic circuitry to fluids. By sealing the electronic circuitry in a hermetically sealed casing 226, the electronic circuitry may operate without risk of short circuiting by the surrounding fluids. Also shown in FIG. 2 are pads 228 to which the input and output lines of the electronic circuitry may be connected. The electronic circuitry itself may be fabricated in a variety of ways. According to an embodiment, the electronic circuitry may be fabricated as an integrated circuit using techniques common in the industry.

Figure 3:
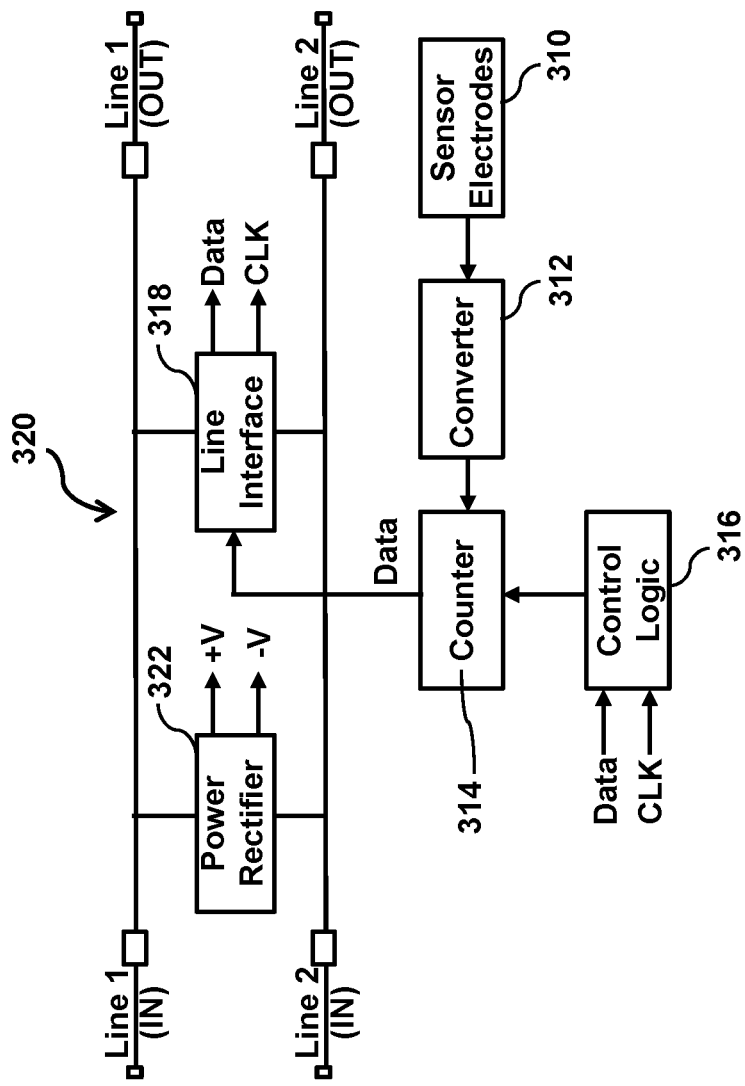
FIG. 3 illustrates a block diagram of a sensor electronics device and a sensor including a plurality of electrodes.

FIG. 3 illustrates a general block diagram of an electronic circuit for sensing an output of a sensor according to one embodiment. At least one pair of sensor electrodes 310 may interface to a data converter 312, the output of which may interface to a counter 314. The counter 314 may be controlled by control logic 316. The output of the counter 314 may connect to a line interface 318. The line interface 318 may be connected to input and output lines 320 and may also connect to the control logic 316. The input and output lines 320 may also be connected to a power rectifier 322.

The sensor electrodes 310 may be used in a variety of sensing applications and may be configured in a variety of ways. For example, the sensor electrodes 310 may be used in physiological parameter sensing applications in which some type of biomolecule is used as a catalytic agent. For example, the sensor electrodes 310 may be used in a glucose and oxygen sensor having a GOx enzyme catalyzing a reaction with the sensor electrodes 310. The sensor electrodes 310, along with a biomolecule or some other catalytic agent, may be placed in a human body in a vascular or non-vascular environment. For example, the sensor electrodes 310 and biomolecule may be placed in a vein and be subjected to a blood stream.

Figure 4:
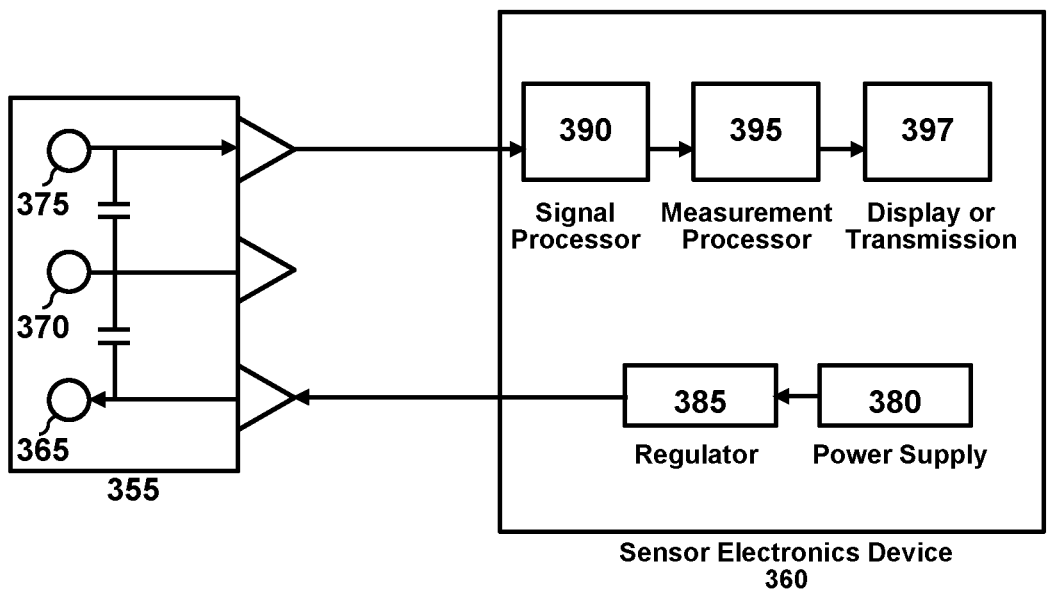
FIG. 4 illustrates an alternative embodiment of the invention including a sensor and a sensor electronics device.
Figure 4:
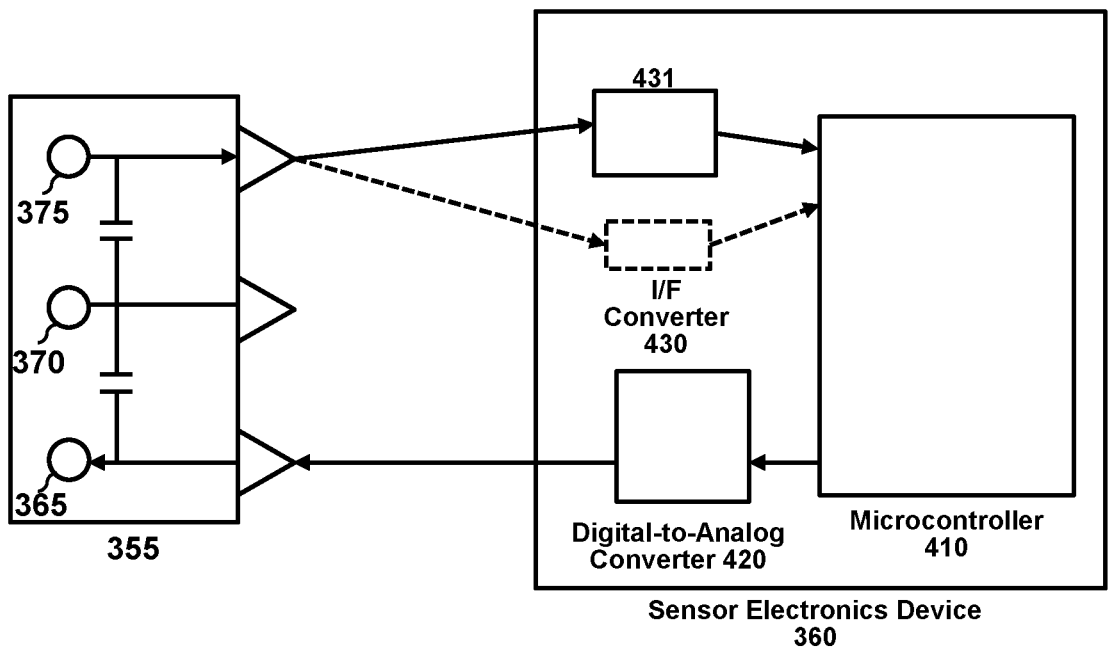

FIG. 4 illustrates a block diagram of a sensor electronics device and a sensor including a plurality of electrodes according to an embodiment herein. FIG. 4 includes system 400. System 400 includes a sensor 355 and a sensor electronics device 360. The sensor 355 includes a counter electrode 365, a reference electrode 370, and a working electrode 375. The sensor electronics device 360 includes a power supply 380, a regulator 385, a signal processor 390, a measurement processor 395, and a display/transmission module 397. The power supply 380 provides power (in the form of either a voltage, a current, or a voltage including a current) to the regulator 385. The regulator 385 transmits a regulated voltage to the sensor 355. In one embodiment, the regulator 385 transmits a voltage to the counter electrode 365 of the sensor 355.

The sensor 355 creates a sensor signal indicative of a concentration of a physiological characteristic being measured. For example, the sensor signal may be indicative of a blood glucose reading. In an embodiment utilizing subcutaneous sensors, the sensor signal may represent a level of hydrogen peroxide in a subject. In an embodiment where blood or cranial sensors are utilized, the amount of oxygen is being measured by the sensor and is represented by the sensor signal. In an embodiment utilizing implantable or long-term sensors, the sensor signal may represent a level of oxygen in the subject. The sensor signal is measured at the working electrode 375. In one embodiment, the sensor signal may be a current measured at the working electrode. In an embodiment, the sensor signal may be a voltage measured at the working electrode.

The signal processor 390 receives the sensor signal (e.g., a measured current or voltage) after the sensor signal is measured at the sensor 355 (e.g., the working electrode). The signal processor 390 processes the sensor signal and generates a processed sensor signal. The measurement processor 395 receives the processed sensor signal and calibrates the processed sensor signal utilizing reference values. In one embodiment, the reference values are stored in a reference memory and provided to the measurement processor 395. The measurement processor 395 generates sensor measurements. The sensor measurements may be stored in a measurement memory (not shown) or by circuitry (e.g., storage circuitry). The sensor measurements may be sent to a display/transmission device to be either displayed on a display in a housing with the sensor electronics or transmitted to an external device.

The sensor electronics device 360 may be a monitor which includes a display to display physiological characteristics readings. The sensor electronics device 360 may also be installed in a desktop computer, a pager, a television including communications capabilities, a laptop computer, a server, a network computer, a personal digital assistant (PDA), a portable telephone including computer functions, an infusion pump including a display, a glucose sensor including a display, and/or a combination infusion pump/glucose sensor. The sensor electronics device 360 may be housed in a blackberry, a network device, a home network device, or an appliance connected to a home network.

FIG. 4 also includes system 450. System 450 includes a sensor electronics device 360 and a sensor 355. The sensor includes a counter electrode 365, a reference electrode 370, and a working electrode 375. The sensor electronics device 360 includes a microcontroller 410 and a digital-to-analog converter (DAC) 420. The sensor electronics device 360 may also include a current-to-frequency converter (I/F converter) 430.

The microcontroller 410 includes software program code, which when executed, or programmable logic which, causes the microcontroller 410 to transmit a signal to the DAC 420, where the signal is representative of a voltage level or value that is to be applied to the sensor 355. The DAC 420 receives the signal and generates the voltage value at the level instructed by the microcontroller 410. In one embodiment, the microcontroller 410 may change the representation of the voltage level in the signal frequently or infrequently. Illustratively, the signal from the microcontroller 410 may instruct the DAC 420 to apply a first voltage value for one second and a second voltage value for two seconds.

The sensor 355 may receive the voltage level or value. In one embodiment, the counter electrode 365 may receive the output of an operational amplifier which has as inputs the reference voltage and the voltage value from the DAC 420. The application of the voltage level causes the sensor 355 to create a sensor signal indicative of a concentration of a physiological characteristic being measured. In an embodiment, the microcontroller 410 may measure the sensor signal (e.g., a current value) from the working electrode. Illustratively, a sensor signal measurement circuit 431 may measure the sensor signal. In an embodiment, the sensor signal measurement circuit 431 may include a resistor and the current may be passed through the resistor to measure the value of the sensor signal. In an embodiment, the sensor signal may be a current level signal and the sensor signal measurement circuit 431 may be a current-to-frequency (I/F) converter 430. The current-to-frequency converter 430 may measure the sensor signal in terms of a current reading, convert it to a frequency-based sensor signal, and transmit the frequency-based sensor signal to the microcontroller 410. In some embodiments, the microcontroller 410 may be able to receive frequency-based sensor signals easier than non-frequency-based sensor signals. The microcontroller 410 receives the sensor signal, whether frequency-based or non-frequency-based, and determines a value for the physiological characteristic of a subject, such as a blood glucose level. The microcontroller 410 may include program code, which when executed or run, is able to receive the sensor signal and convert the sensor signal to a physiological characteristic value. In one embodiment, the microcontroller 410 may convert the sensor signal to a blood glucose level. In an embodiment, the microcontroller 410 may utilize measurements stored within an internal memory or by circuitry (e.g., storage circuitry) in order to determine the blood glucose level of the subject. In an embodiment, the microcontroller 410 may utilize measurements stored within a memory external to the microcontroller 410 or by circuitry to assist in determining the blood glucose level of the subject.

After the physiological characteristic value is determined by the microcontroller 410, the microcontroller 410 may store measurements of the physiological characteristic values for a number of time periods. For example, a blood glucose value may be sent to the microcontroller 410 from the sensor every second or five seconds, and the microcontroller may save sensor measurements for five minutes or ten minutes of BG readings. The microcontroller 410 may transfer the measurements of the physiological characteristic values to a display on the sensor electronics device 360. For example, the sensor electronics device 360 may be a monitor which includes a display that provides a blood glucose reading for a subject. In one embodiment, the microcontroller 410 may transfer the measurements of the physiological characteristic values to an output interface of the microcontroller 410. The output interface of the microcontroller 410 may transfer the measurements of the physiological characteristic values, e.g., blood glucose values, to an external device, e.g., an infusion pump, a combined infusion pump/glucose meter, a computer, a personal digital assistant, a pager, a network appliance, a server, a cellular phone, or any computing device.

Figure 5:
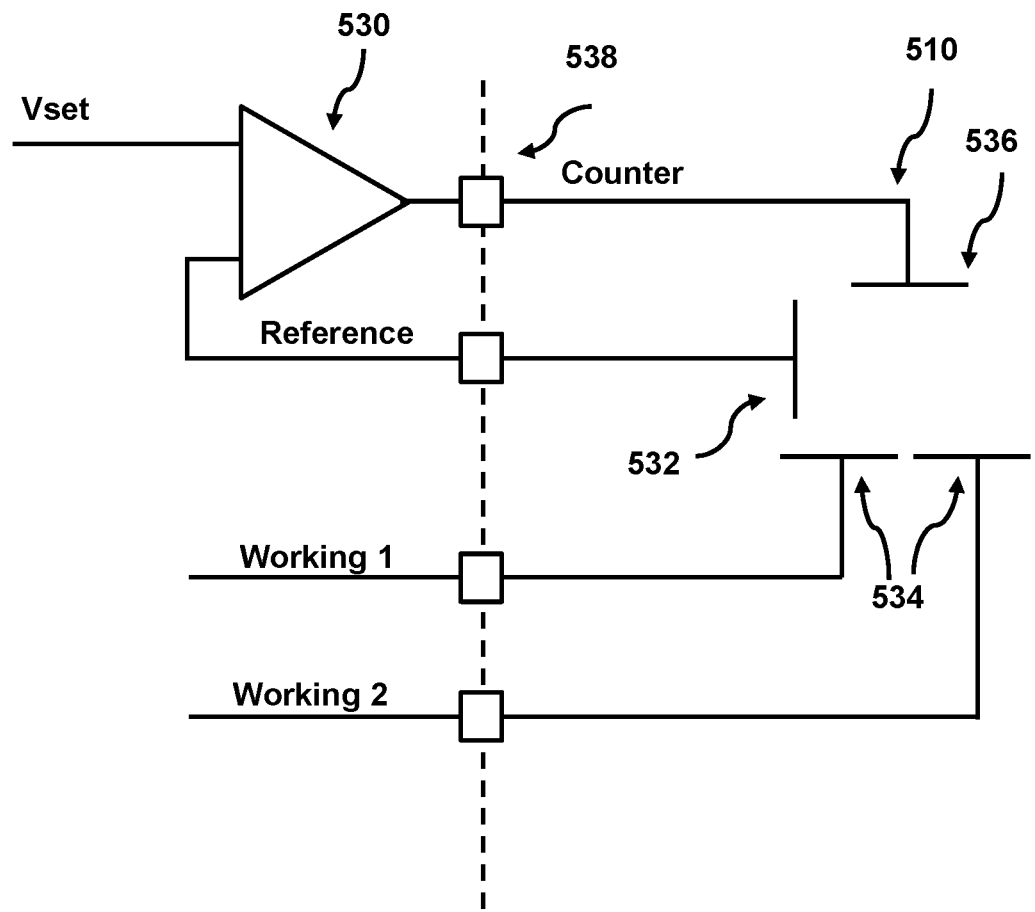
FIG. 5 illustrates an electronic block diagram of the sensor electrodes and a voltage being applied to the sensor electrodes.

FIG. 5 illustrates an electronic block diagram of the sensor electrodes and a voltage being applied to the sensor electrodes according to an embodiment. In some embodiments, FIG. 5 may illustrate an electrode with a GOx sensor and/or an electrode capable of sensing GOx. For example, FIG. 5 may illustrate a working electrode with a GOx sensor that functions with a background electrode in which the background electrode has no GOx sensor (e.g., as discussed below in relation to FIGS. 8 and 9). The system may then compare the first signal and the second signal to detect ingestion of a medication by the user. The system may generate a sensor glucose value based on the comparison. In the embodiment illustrated in FIG. 5, an op amp 530 or other servo-controlled device may connect to sensor electrodes 510 through a circuit/electrode interface 538. The op amp 530, utilizing feedback through the sensor electrodes, attempts to maintain a prescribed voltage (what the DAC may desire the applied voltage to be) between a reference electrode 532 and a working electrode 534 by adjusting the voltage at a counter electrode 536. Current may then flow from a counter electrode 536 to a working electrode 534. Such current may be measured to ascertain the electrochemical reaction between the sensor electrodes 510 and the biomolecule of a sensor that has been placed in the vicinity of the sensor electrodes 510 and used as a catalyzing agent. The circuitry (e.g., processing circuitry) disclosed in FIG. 5 may be utilized in a long-term or implantable sensor or may be utilized in a short-term or subcutaneous sensor.

In a long-term sensor embodiment, where a GOx enzyme is used as a catalytic agent in a sensor, current may flow from the counter electrode 536 to a working electrode 534 only if there is oxygen in the vicinity of the enzyme and the sensor electrodes 510. Illustratively, if the voltage set at the reference electrode 532 is maintained at about 0.5 volts, the amount of current flowing from the counter electrode 536 to a working electrode 534 has a fairly linear relationship with unity slope to the amount of oxygen present in the area surrounding the enzyme and the electrodes. Thus, increased accuracy in determining an amount of oxygen in the blood may be achieved by maintaining the reference electrode 532 at about 0.5 volts and utilizing this region of the current-voltage curve for varying levels of blood oxygen. Different embodiments may utilize different sensors having biomolecules other than a glucose oxidase enzyme and may, therefore, have voltages other than 0.5 volts set at the reference electrode.

As discussed above, during initial implantation or insertion of the sensor 510, the sensor 510 may provide inaccurate readings due to the adjusting of the subject to the sensor and also electrochemical byproducts caused by the catalyst utilized in the sensor. A stabilization period is needed for many sensors in order for the sensor 510 to provide accurate readings of the physiological parameter of the subject. During the stabilization period, the sensor 510 does not provide accurate blood glucose measurements. Users and manufacturers of the sensors may desire to improve the stabilization timeframe for the sensor so that the sensors can be utilized quickly after insertion into the subject's body or a subcutaneous layer of the subject.

In previous sensor electrode systems, the stabilization period or timeframe was one hour to three hours. In order to decrease the stabilization period or timeframe and increase the timeliness of accuracy of the sensor, a sensor (or electrodes of a sensor) may be subjected to a number of pulses rather than the application of one pulse followed by the application of another voltage, for the second time period. In one embodiment, the first voltage may be 1.07 volts. In an embodiment, the first voltage may be 0.535 volts. In an embodiment, the first voltage may be approximately 0.7 volts.

Figure 6:
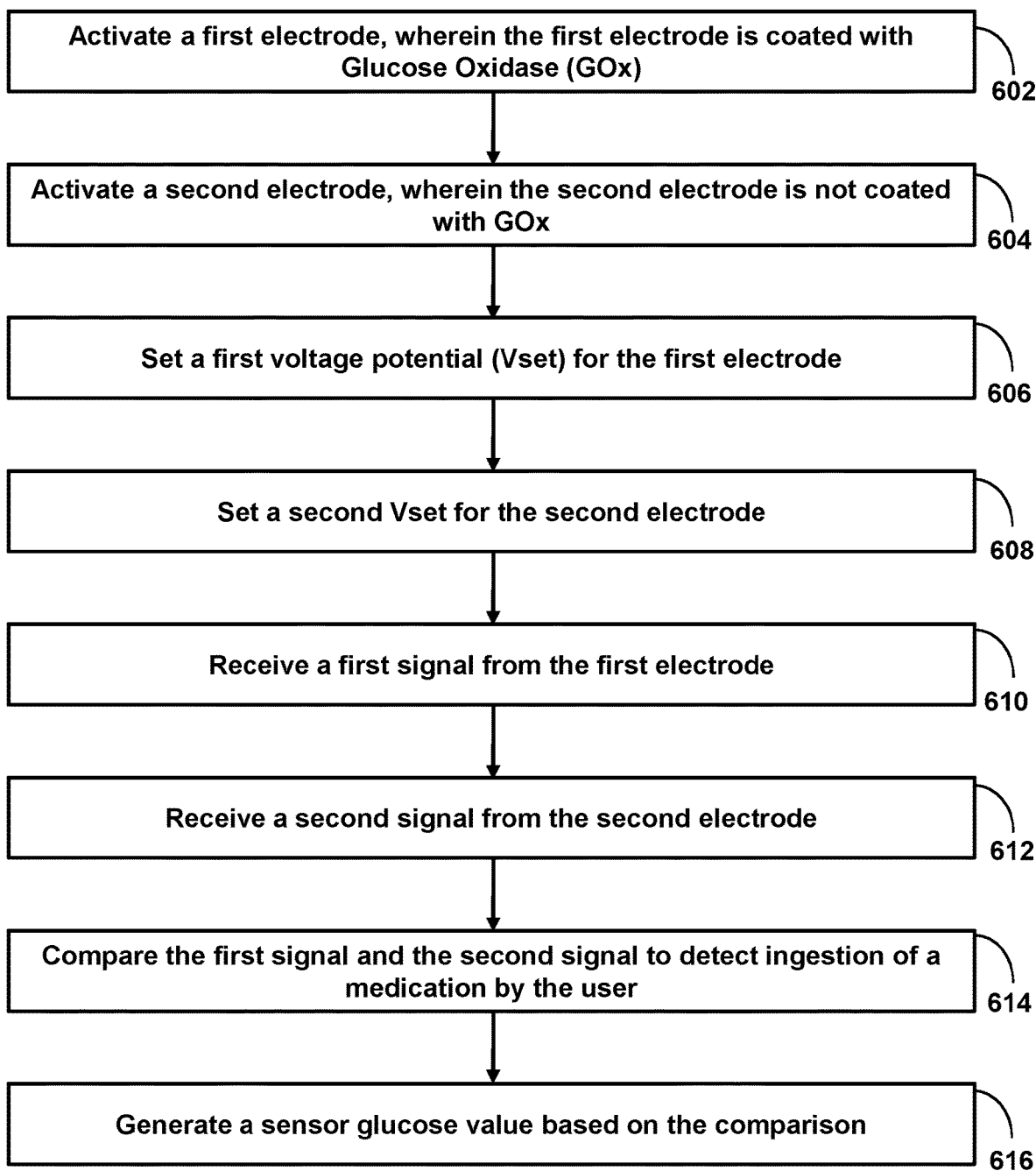
FIG. 6 shows a flowchart of the steps involved in continuous glucose monitoring, in accordance with one or more embodiments.

FIG. 6 shows a flowchart of the steps involved in continuous glucose monitoring, in accordance with one or more embodiments. For example, process 600 may represent the steps taken by one or more devices as shown in FIGS. 1-5.

At step 602, process 600 (e.g., using circuitry described in FIGS. 1-5) activates a first electrode on a user, wherein the first electrode detects Glucose Oxidase (GOx). For example, the system may activate a first electrode on a user (e.g., a patient), wherein the first electrode detects Glucose Oxidase (GOx) (e.g., the first electrode includes a GOx sensor).

For example in some embodiments, a sensor may initiate a start-up procedure either based on a remotely received command, automatically (e.g., based another sensor detecting certain conditions), or from a user inputted command. In response to the sensor start up, a first and second electrode (e.g., corresponding to a working electrode and a background electrode). Additionally, the first and second electrode may undergo a current and/or voltage initialization sequence. These initialization sequences may differ based on whether or not an electrode includes a GOx sensor.

At step 604, process 600 (e.g., using circuitry described in FIGS. 1-5) activates a second electrode on the user, wherein the second electrode does not detect GOx. For example, the system may activate a second electrode on the user, wherein the second electrode does not detect GOx. For example, the second electrode may not include a GOx sensor.

At step 606, process 600 (e.g., using circuitry described in FIGS. 1-5) sets a first voltage potential (Vset) for the first electrode. For example, the system may set, using the control circuitry, a first voltage potential (Vset) for the first electrode. For example, the first Vset may be in a range of 400-500 mV.

At step 608, process 600 (e.g., using circuitry described in FIGS. 1-5) sets a second Vset for the second electrode. For example, the system may set, using the control circuitry, a second voltage potential (Vset) for the second electrode. In some examples, the first Vset may be lower than the second Vset. For example, the second Vset may be in a range of 500-600 mV.

At step 610, process 600 (e.g., using circuitry described in FIGS. 1-5) receives a first signal from the first electrode. For example, the system may receive, using the control circuitry, a first signal from the first electrode. The first electrode may be a working electrode, and the system may receive a 5-minute reading of sensor current in nA, sometimes called "raw Isig," or other Isig value (e.g., as shown above).

At step 612, process 600 (e.g., using circuitry described in FIGS. 1-5) receive a second signal from the second electrode. For example, the system may receive, using the control circuitry, a second signal from the second electrode. The second electrode may be a background electrode, and the system may receive a 5-minute reading of sensor current in nA, sometimes called "raw Isig," or other Isig value (e.g., as shown above).

At step 614, process 600 (e.g., using circuitry described in FIGS. 1-5) compares the first signal and the second signal to detect ingestion of a medication by the user. For example, the system may compare, using the control circuitry, the first signal and the second signal to detect ingestion of a medication by the user. For example, the medication (e.g., acetaminophen) may produce an interfering current that increases a glucose reading.

In some embodiments, comparing the first signal and the second signal to detect ingestion of a medication by the user further comprises one or more steps. For example, the system may determine a noise level for the second signal. The system may compare the noise level to a noise threshold. The system may calculate the sensor glucose value based on the second signal in response to the noise level not exceeding the noise threshold. For example, the system may calculate a sensor glucose value based on the first electrode using the Isig from the first electrode.

In another example, the system may determine a noise level for the second signal. The system may compare the noise level to a noise threshold. The system may calculate the sensor glucose value based on a modified first signal, wherein the modified first signal is based on a weighted difference between the first signal and the second signal. For example, the system may apply a scale factor to the Isig of the second electrode and apply a Scale factor to the Isig. In some embodiments, the scale factor may be a linear or non-linear multidimensional scale factor. The system may then determine a difference between the Isig of the first electrode and scaled Isig of the second electrode. The system may then calculate a sensor glucose value in mg/dL based on the difference between the Isig of the first electrode and scaled Isig of the second electrode. The sensor glucose value may then be used to display a value to the user.

The normalized values are scaled using scaling functions, specific to the environmental or physiological factor under consideration, and the scaled values are combined to generate an aggregate value. In one embodiment, the combination may be obtained by multiplying the different scaled values together. In other embodiments, the aggregation may be achieved by determining a mean value or selecting the maximum of the available values.

It is noted that the threshold values, or ranges, for the above-mentioned parameters may depend on various factors, including the specific sensor and/or electrode design. Nevertheless, in one embodiment, typical ranges for some of the above-mentioned parameters may be, e.g., as follows: Bound threshold for 1 kHz real impedance=[0.3e+4 2e+4]; Bound threshold for 1 kHz imaginary impedance=[−2e+3, 0]; Bound threshold for 0.105 Hz real impedance=[2e+4 7e+4]; Bound threshold for 0.105 Hz imaginary impedance= [−2e+5-0.25e+5]; and Bound threshold for Nyquist slope=[2 5]. Noise may be calculated, e.g., using second order central difference method where, if noise is above a certain percentage (e.g., 30%) of median value for each variable buffer, it is considered to be out of noise bound.

It should also be noted that, in further embodiments, in determining whether data should be blanked, or the sensor terminated, the logic may also consider, in addition to the above-mentioned thresholds, sudden increases in impedance by, e.g., comparing impedance derivatives to historical derivatives. Moreover, the algorithm may incorporate noise-based blanking or termination, depending on the duration of high noise-low sensor signal combination. In this regard, prior methodologies included termination of the sensor after three (3) consecutive 2-hour windows of high noise and low sensor signal. However, in order to prevent unreliable data from being displayed to the user, embodiments employ noise-based blanking, wherein the algorithm stops calculating SG values after 2 consecutive 2-hour windows (i.e., at the start of the third consecutive window) involving high noise and low signal. In further aspects, the algorithm may allow further calculation and display of the calculated SG values after one hour of blanking, rather than two hours, where the sensor signal appears to have recovered. This is an improvement over methodologies that blank otherwise reliable data for longer periods of time.

At step 616, process 600 (e.g., using circuitry described in FIGS. 1-5) generates a sensor glucose value based on the comparison. For example, the system may generate, using the control circuitry, a sensor glucose value based on the comparison. For example, the system may generate the sensor glucose value on a user interface and/or be used to adjust a glucose amount delivered to the user. For example, embodiments are directed to assessment of reliability of sensor glucose values, as well as estimation of sensor-data error direction, in order to provide users and automated insulin delivery systems—including those in closed-loop systems—an indicator of how reliable the system is when SG is displayed to the user. Depending on the reliability of sensor data, such automated systems are then able to assign a corresponding weight to the SG and make a determination as to how aggressively treatments should be provided to users. Additionally, the direction of error can also be used to inform users and/or the insulin delivery system in connection with SG being a "false low" or a "false high" value. The foregoing may be achieved by, e.g., detecting dips in sensor data during the first day (EIS dip detection), detecting sensor lag, and lower-frequency (e.g., 10 Hz) impedance changes.

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 2-4 could be used to perform one or more of the steps in FIG. 6.

Figure 7:
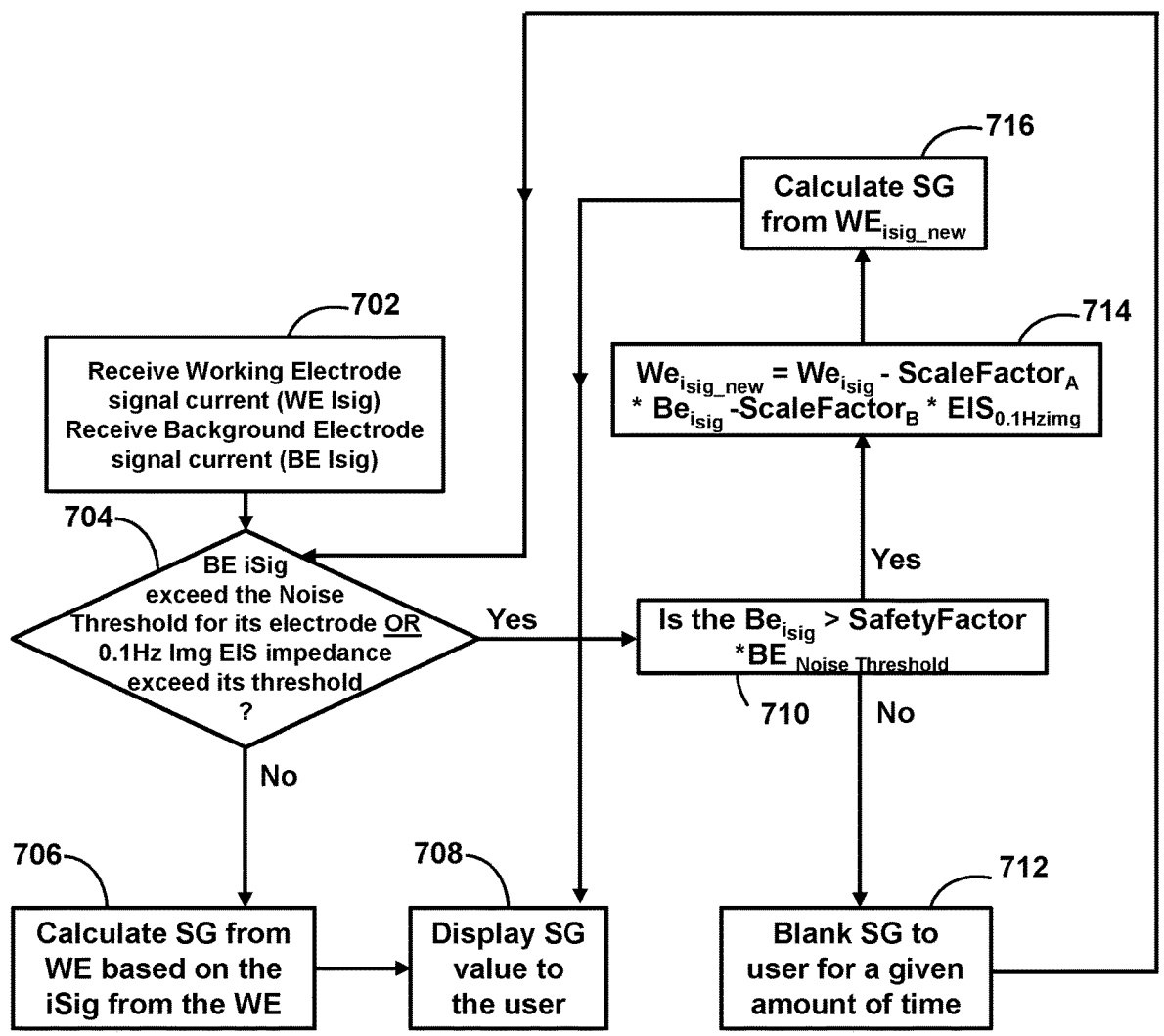
FIG. 7 shows a flowchart of the steps involved in continuous glucose monitoring, in accordance with one or more embodiments.

FIG. 7 shows a flowchart of the steps involved in continuous glucose monitoring, in accordance with one or more embodiments. For example, process 700 may represent the steps taken by one or more devices as shown in FIGS. 1-5.

At step 702, process 700 (e.g., using circuitry described in FIGS. 1-5) receives a first and second signal (e.g., respective Isigs) from a first and second electrode (e.g., a working electrode and a background electrode). For example, the system may use one or more steps as described above in FIG. 6 to generate the Isigs.

At step 704, process 700 (e.g., using circuitry described in FIGS. 1-5) determines whether an Isig for a background electrode (e.g., the second electrode of FIG. 6) exceeds a noise threshold for the background electrode or has a 0.1 Hz IMG EIS Impedance ("EIS value") exceed its threshold. For example, the effective resistance of an electric circuit or component to alternating current, arising from the combined effects of ohmic resistance and reactance of the EIS may be compared to a respective threshold.

EIS may be used in sensor systems where the sensor includes a single working electrode, as well those in which the sensor includes multiple (redundant) working electrodes. In one embodiment, EIS provides valuable information regarding the age (or aging) of the sensor. Specifically, at different frequencies, the magnitude and the phase angle of the impedance vary. Additionally, EIS may enable detection of sensor failure by detecting when the sensor's impedance drops below a low impedance threshold level indicating that the sensor may be too worn to operate normally. The system may then terminate the sensor before the specified operating life. Sensor impedance can also be used to detect other sensor failure (modes). For example, when a sensor goes into a low-current state (i.e., sensor failure) due to any variety of reasons, the sensor impedance may also increase beyond a certain high impedance threshold. If the impedance becomes abnormally high during sensor operation, due, e.g., to protein or polypeptide fouling, macrophage attachment or any other factor, the system may also terminate the sensor before the specified sensor operating life.

If process 700 determine that neither criteria is met, process 700 proceeds to step 706. If process 700 determine that either criteria is met, process 700 proceeds to step 710.

At step 706, process 700 (e.g., using circuitry described in FIGS. 1-5) calculates a sensor glucose value from the working electrode based on the Isig from the working electrode and displays the value to the user at step 708.

At step 710, process 700 (e.g., using circuitry described in FIGS. 1-5) determines if the Isig from the background electrode (e.g., the second electrode of FIG. 6 above) is greater than a weighted background electrode noise threshold. For example, to determine the weighted background electrode noise threshold, the system may apply a safety factor to the background electrode noise threshold. If the Isig for the background electrode is greater, process 700 proceeds to step 714. If the Isig for the background electrode is not greater, process 700 proceeds to step 712. In some examples, steps 710 and 712 are optional and process 700 continues to step 714 from the YES branch of step 704.

At step 712, process 700 (e.g., using circuitry described in FIGS. 1-5) blanks the sensor glucose value to the user for a given amount of time and returns to step 704. It should also be noted that, in further embodiments, in determining whether data should be blanked, or the sensor terminated, the logic may also consider, in addition to the above-mentioned thresholds, sudden increases in impedance by, e.g., comparing impedance derivatives to historical derivatives. Moreover, the algorithm may incorporate noise-based blanking or termination, depending on the duration of high noise-low sensor signal combination. In this regard, prior methodologies included termination of the sensor after three (3) consecutive 2-hour windows of high noise and low sensor signal. However, in order to prevent unreliable data from being displayed to the user, embodiments employ noise-based blanking, wherein the algorithm stops calculating SG values after 2 consecutive 2-hour windows (i.e., at the start of the third consecutive window) involving high noise and low signal. In further aspects, the algorithm may allow further calculation and display of the calculated SG values after one hour of blanking, rather than two hours, where the sensor signal appears to have recovered. This is an improvement over methodologies that blank otherwise reliable data for longer periods of time.

At step 714, process 700 (e.g., using circuitry described in FIGS. 1-5) determines a new Isig value for the working electrode using a pre-determined mathematical model (e.g., as shown by the formula at step 714). For example, the new value is the difference between the Isig value for the working electrode and a weighted Isig for the background electrode and a weighted EIS value. In some examples, the new value is the difference between the Isig value for the working electrode and a weighted Isig value for the background electrode. Process 700 may then proceed to step 716 and calculate a new sensor glucose value based on the new Isig value for the working electrode before returning to step 704.

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Furthermore, it should be noted that any of the devices or equipment discussed in relation to FIGS. 2-4 could be used to perform one or more of the steps in FIG. 7.

Figure 8:
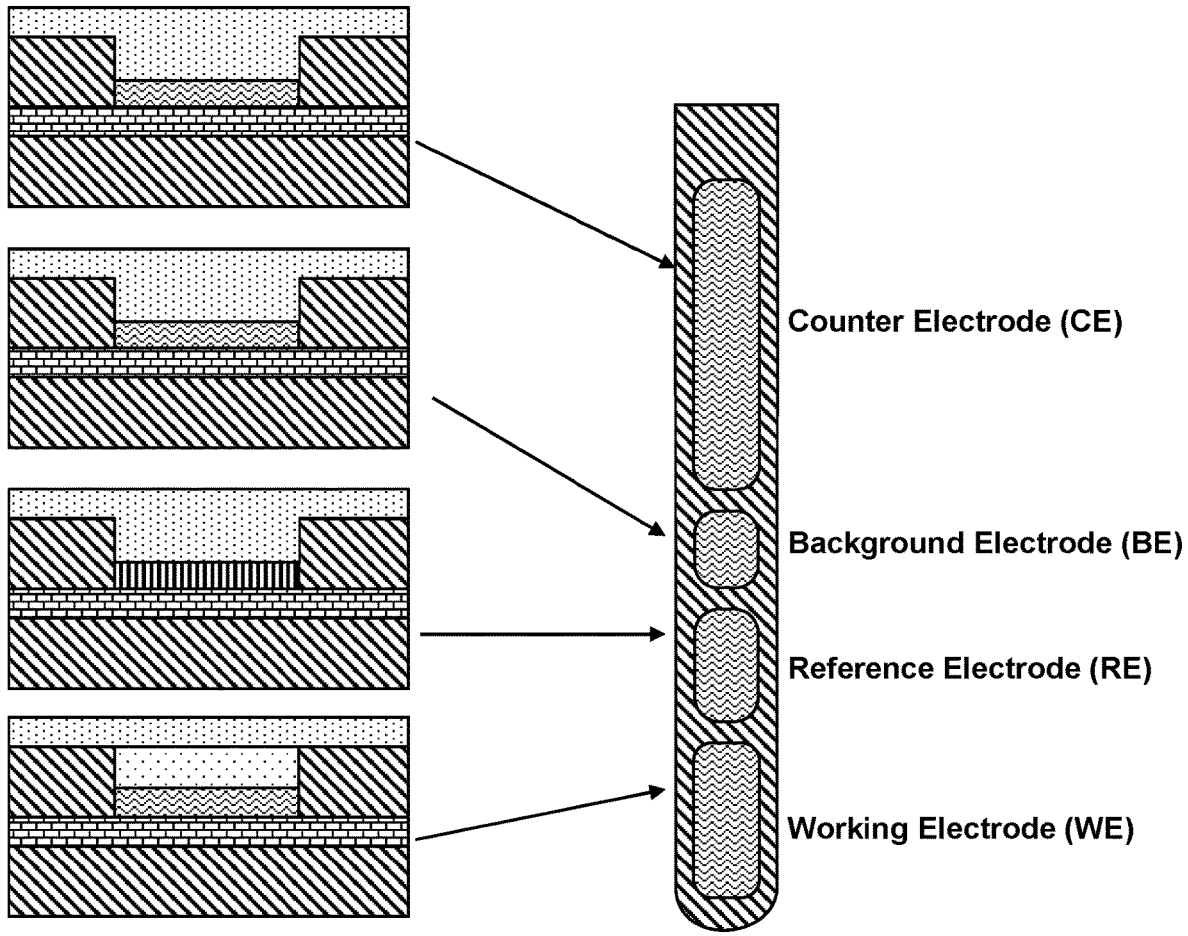
FIG. 8 illustrates a unit sensor having a background electrode metal layer made of platinum.

FIG. 8 illustrates a unity sensor having a background electrode metal layer made of platinum. As shown in FIG. 8, the sensor may comprise a conductor trace (e.g., gold) surrounded by an insulating material (e.g., polyimide). In some embodiments, the sensor may include a counter electrode, background electrode, reference electrode, working electrode, and/or other electrodes. In some embodiments, each electrode may comprise platinum, gold, and/or other materials. For example, the reference electrode may include silver or silver-chloride and the working electrode may include GOx. In some embodiments, the background electrode (e.g., comprising platinum in this embodiment) may be distinguishable from the working electrode in that the background electrode may not include GOx. In some embodiments, each electrode may be coated in a glucose limiting membrane. In some embodiments, a unity sensor as shown in FIG. 8 may be included in a CGM device (e.g., as discussed in relation to FIG. 10).

Figure 9:
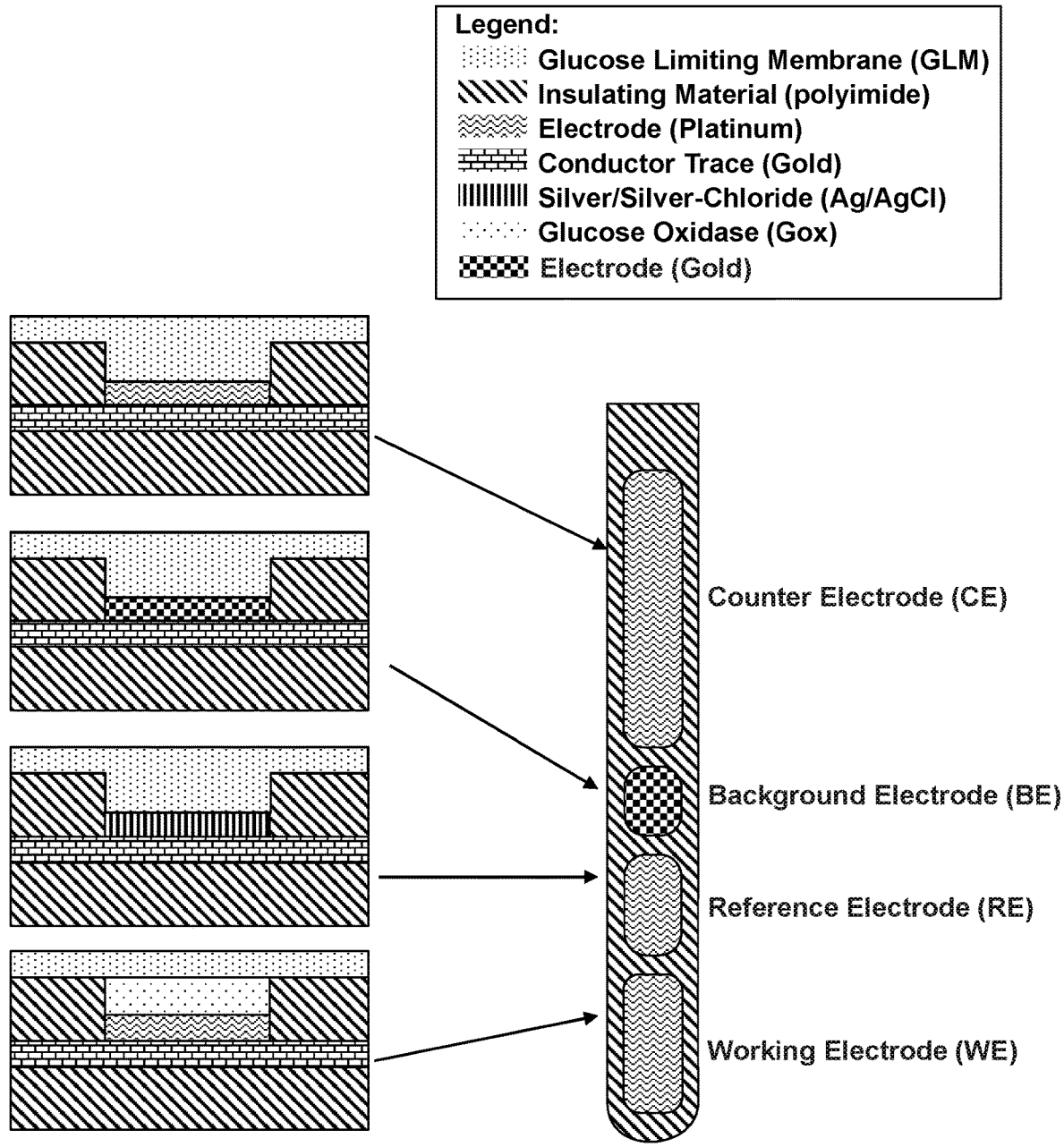
FIG. 9 illustrates a unity sensor having a background electrode metal layer made of gold.

FIG. 9 illustrates a unity sensor having a background electrode metal layer made of gold. As shown in FIG. 9, the sensor may comprise a conductor trace (e.g., gold) surrounded by an insulating material (e.g., polyimide). In some embodiments, the sensor may include a counter electrode, background electrode, reference electrode, working electrode, and/or other electrodes. In some embodiments, each electrode may comprise platinum, gold, and/or other materials. For example, the reference electrode may include silver or silver-chloride and the working electrode may include GOx. In some embodiments, the background electrode (e.g., comprising gold in this embodiment) may be distinguishable from the working electrode in that the background electrode may not include GOx. In some embodiments, each electrode may be coated in a glucose limiting membrane. In some embodiments, a unity sensor as shown in FIG. 9 may be included in a CGM device (e.g., as discussed in relation to FIG. 10).

Figure 10:
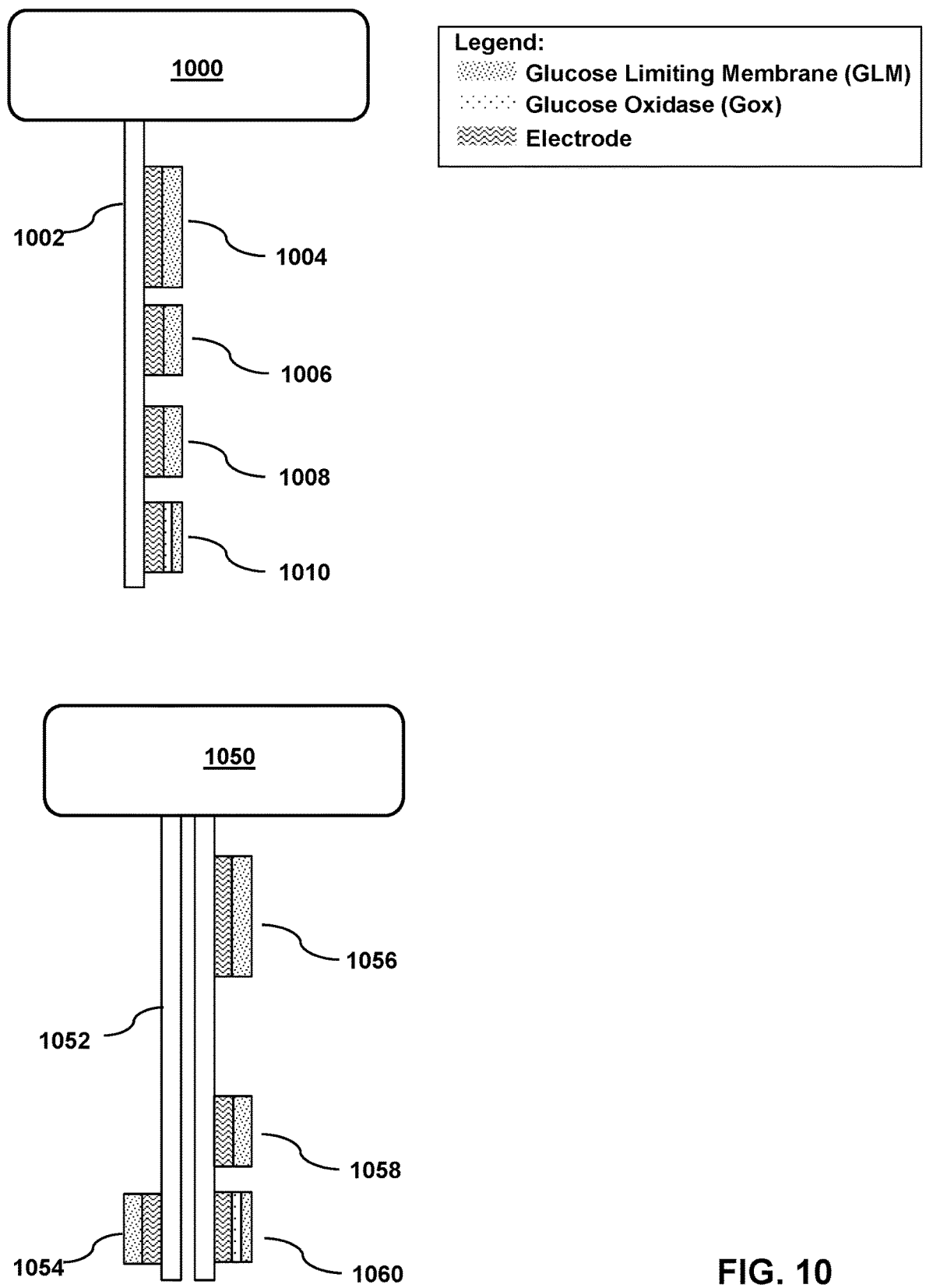
FIG. 10 illustrates a single sensor flex in a CGM device and a dual sensor flex in a CGM device.

FIG. 10 illustrates a single sensor flex 1002 in a CGM device 1000 and a dual sensor flex 1052 in a CGM device 1050. Single sensor flex 1002 (e.g., as shown in FIG. 8) may include a counter electrode 1004, background electrode 1006, reference electrode 1008, working electrode 1010, and/or other electrodes. The dual sensor flex 1052 includes two sensor flexes (e.g., as shown in FIG. 9) in CGM device 1050. For example, one sensor of dual sensor flex 1052 may include a counter electrode 1056, reference electrode 1058, working electrode 1060, and/or other electrodes, while the other sensor of dual sensor flex 1052 may include a background electrode 1054 and/or other electrodes. As shown in FIG. 10, the two sensor flexes in the dual sensor flex may be placed back-to-back in CGM device 1050. In some embodiments, GOx may be deposited onto one or more of the electrodes shown in FIG. 10. In some embodiments, a different enzyme of interest may be deposited onto one or more electrodes. In some embodiments, a glucose limiting membrane (GLM) may be deposited on top of the GOx (or other enzyme) layer. In some embodiments, the GOx and GLM layers may be deposited onto certain electrodes and may not be deposited onto other electrodes. For example, the GOx and GLM layers may be deposited onto the working electrode but not onto other electrodes. In some embodiments, the deposited layers may not be deposited solely above the electrodes. For example, the GLM layer may extend from one electrode to another.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

1. A method for continuous glucose monitoring, the method comprising: activating a first electrode on a user; activating a second electrode the user; setting the first electrode to a first voltage potential (Vset); setting the second electrode to a second voltage potential (Vset); receiving a first signal from the first electrode; receiving a second signal from the second electrode; comparing the first signal and the second signal to detect ingestion of a medication by the user; and generating a sensor glucose value based on the comparison.
2. The method of embodiment 1, wherein the medication produces an interfering current that increases a glucose reading at the first electrode.
3. The method of any of embodiments 1-2, further comprising: storing the first voltage potential (Vset) for the first electrode, wherein the first electrode detects Glucose Oxidase (GOx); storing the second voltage potential (Vset) for the second electrode, wherein the second electrode does not detect GOx; and wherein the first Vset is lower than the second Vset.
4. The method of any of embodiments 1-3, further comprising inputting the first signal and the second signal as parameters in a pre-determined mathematical model for adjusting the sensor glucose value.
5. The method of any of embodiments 1-4, further comprising selecting a material of the first electrode, a material of the second electrode, or an applied voltage based on an analyte.
6. The method of any of embodiments 1-5, wherein the first electrode and the second electrode are located on a single sensor or on separate sensors in a device.
7. The method of any of embodiments 1-6, wherein comparing the first signal and the second signal to detect ingestion of the medication by the user comprises: determining a noise level for the second signal; comparing the noise level to a noise threshold; and calculating the sensor glucose value based on the second signal in response to the noise level not exceeding the noise threshold.
8. The method of any of embodiments 1-7, wherein comparing the first signal and the second signal to detect ingestion of the medication by the user comprises: determining a noise level for the second signal; comparing the noise level to a noise threshold; and calculating the sensor glucose value based on a modified first signal, wherein the modified first signal is based on a weighted difference between the first signal and the second signal.

9. A tangible, non-transitory, machine-readable medium storing instructions that, when executed by a data processing apparatus, cause the data processing apparatus to perform operations comprising those of any of embodiments 1-8.

10. A system comprising: one or more processors; and memory storing instructions that, when executed by the processors, cause the processors to effectuate operations comprising those of any of embodiments 1-8.

11. A system comprising means for performing any of embodiments 1-8.

What is claimed is:

1. A system for continuous glucose monitoring, comprising:
one or more processors; and
one or more processor-readable media storing instructions which, when executed by the one or more processors, causes the system to:
activate a working electrode of a subcutaneously placed glucose sensor, the working electrode configured to generate a first sensor current;
activate a background electrode of the subcutaneously placed glucose sensor, the background electrode configured to generate a second sensor current;
cause a plurality of pulses to be applied to the working electrode and the background electrode to stabilize the glucose sensor;
set the working electrode to a first voltage potential, wherein the working electrode includes a glucose oxidase sensor and the first sensor current generated by the working electrode is affected by exposure of the glucose oxidase sensor to a medication ingested by a user;
set the background electrode to a second voltage potential greater than the first voltage potential, the background electrode having a metallization layer, wherein the second sensor current generated by the background electrode is not affected by exposure of the background electrode to the medication ingested by the user;
receive the first sensor current from the working electrode;
receive the second sensor current from the background electrode;
generate a sensor glucose value based on the first sensor current;
determine an electrochemical impedance spectroscopy (EIS) impedance value of the background electrode;
input the first sensor current and the second sensor current into a mathematical model that calculates a new value of the first sensor current based at least in part on the EIS impedance value of the background electrode; and
adjust the sensor glucose value based on the new value of the first sensor current calculated by the mathematical model.

2. The system of claim 1, wherein the glucose sensor includes a first flex sensor configured for subcutaneous placement within the user and a second flex sensor disposed separate from the first flex sensor and configured for subcutaneous placement within the user.

3. The system of claim 2, the working electrode is disposed on the first flex sensor of the glucose sensor and the background electrode is disposed on the second flex sensor of the glucose sensor.

4. The system of claim 3, wherein a counter electrode and a reference electrode are disposed on the first flex sensor.

5. The system of claim 4, wherein a glucose limiting membrane is disposed on at least one of the counter electrode, the reference electrode, the background electrode, or the working electrode.

6. A method for continuous glucose monitoring, the method comprising:
activating, using control circuitry, a working electrode of a subcutaneously placed glucose sensor, the working electrode configured to generate a first sensor current;
activating, using the control circuitry, a background electrode of the subcutaneously placed glucose sensor, the background electrode configured to generate a second sensor current;
causing, using the control circuitry, a plurality of pulses to be applied to the working electrode and the background electrode to stabilize the glucose sensor;
setting, using the control circuitry, the working electrode to a first voltage potential, wherein the working electrode includes a glucose oxidase sensor and the first sensor current generated by the working electrode is affected by exposure of the glucose oxidase sensor to a medication ingested by a user;
setting, using the control circuitry, the background electrode to a second voltage potential greater than the first voltage potential, the background electrode having a metallization layer, wherein the second sensor current generated by the background electrode is not affected by exposure of the background electrode to the medication ingested by the user;
receiving, using the control circuitry, the first sensor current from the working electrode;
receiving, using the control circuitry, the second sensor current from the background electrode;
generating, using the control circuitry, a sensor glucose value based on the first sensor current;
determining an electrochemical impedance spectroscopy (EIS) impedance value of the background electrode;
inputting the first sensor current and the second sensor current into a mathematical model that calculates a new value of the first sensor current based at least in part on the EIS impedance value of the background electrode; and
adjusting the sensor glucose value based on the new value of the first sensor current calculated by the mathematical model.

7. The method of claim 6, wherein the medication produces an interfering current that increases a glucose reading at the working electrode.

8. The method of claim 6, further comprising selecting a material of the working electrode, a material of the background electrode, or an applied voltage based on an analyte.

9. The method of claim 6, wherein:
the glucose sensor includes a first flex sensor and a second flex sensor disposed separate from the first flex sensor;
the working electrode, a counter electrode, and a reference electrode are disposed on the first flex sensor, and the background electrode is disposed on the second flex sensor.

* * * * *